(12) United States Patent
Rowe

(10) Patent No.: US 6,903,100 B2
(45) Date of Patent: Jun. 7, 2005

(54) USE OF REGULARLY SCHEDULED HIGH DOSE INTRAVENOUS METHOTREXATE THERAPY, WITH INTERIM ADMINISTRATION OF IMMUNOMODULATORY AGENTS, TO TREAT MULTIPLE SCLEROSIS AND OTHER DISEASES OF THE CENTRAL NERVOUS SYSTEM

(75) Inventor: Vernon D. Rowe, Kansas City, MO (US)

(73) Assignee: MidAmerica Neuroscience Research Foundation, Kansas City, MO (US)

( * ) Notice: Subject to any disclaimer, the term of this patent is extended or adjusted under 35 U.S.C. 154(b) by 274 days.

(21) Appl. No.: 10/128,947

(22) Filed: Apr. 24, 2002

(65) Prior Publication Data

US 2003/0008875 A1 Jan. 9, 2003

Related U.S. Application Data

(60) Provisional application No. 60/288,567, filed on May 3, 2001.

(51) Int. Cl.[7] .................. A61K 31/525; A61K 31/555; A61K 31/275; A61K 39/38; A61K 45/00
(52) U.S. Cl. ...................... 514/251; 514/186; 514/521; 514/638; 514/742; 424/184.1; 424/279.1
(58) Field of Search ................................. 514/251, 186, 514/521, 903, 889, 638, 742, 825; 424/184.1, 810, 279.1

(56) References Cited

U.S. PATENT DOCUMENTS

| | | | |
|---|---|---|---|
| 5,166,149 A | 11/1992 | Loev | |
| 5,935,577 A | 8/1999 | Weiner et al. | |

OTHER PUBLICATIONS

Uria, D. F., Treatment of Multiple Sclerosis, Neurologia, 1999, 14/Suppl. 6, pp. 1–12, abstract.*
Goodkin, et al., Low Dose (7.5 mg) Oral Methotrexate reduces the rate of progression in chronic progressive multiple sclerosis, Ann Neurol, 1995, 37:30–40.
Weiner, et al., Intermittent Cyclophosphamide Pulse Therapy in Progressive Multiple Sclerosis: Final Report of the Northeast Cooperative Multiple Sclerosis Treatment Group, Neurology, 1993, 43: 910–8.
Cronstein, The Mechanism of Actin of Methotrexate,Rheum Dis Clin North Am, 1997, 23: 739–55.
Glantz, et al., High–Dose Intravenous Methotrexate for Patients With Nonleukemic Sarcoma Leptomeningeal Cancer: Is Intrathecal Chemotherapy Necessary?, J Clin Oncol, 1998, 16: 1561–7.

Pignon, et al., Pharmacokinetics of High–Dose Methotrexate in Adult Osteogenic Sarcoma, Cancer Chemother Pharmacol, 1994, 33: 420–4.
Balis, Remission Induction of Meningeal Leukemia With High–Dose Intravenous Methotrexate, J Clin Oncol, 1985, 3: 485–9.
Doolittle, et al., Safety and Efficacy of a Multicenter Study Using Intraarterial Chemotherapy in Conjunction With Osmotic Opening of the Blood–Brain barrier for the Treatment of Patients With Malignant Brain Tumors, Cancer, 2000, 88: 637–47.
Neuwelt, et al., Primary CNS Lymphoma Treated With Osmotic Blood–Brain Barrier Disruption: Prolonged Survival and Preservation of Cognitive Function, J Clin Oncol, 1991, 9: 1580–90.
Wang, et al., Methotrexate Pulse Therapy on MSFC and Cellular Immunology Markers in Patients With Relapsing Progressive Multiple Sclerosis, Neurology, 2001, 56, Suppl. 3: A365.
Currier, et al., Low Dose Oral Methotrexate Treatment of Multiple Sclerosis: A Pilot Study [published erratum appears in J Neurol Neurosurg Psychiatry Apr. 1999; 57(4): 528]. J Neurosurg Psychiatry, 1993, 56: 1217–8.
Goodkin, et al., Low–Dose Oral Methotrexate in Chronic Progressive Multiple Sclerosis: Analyses of Serial MRIs., Neurology, 1996, 47: 1153–7.
Rensel, et al., Oral Methotrexate Dose Escalation Study in Progressive Multiple Sclerosis, Ann Neurol, 1997, 42: 423.
Tetef, et al., Pharmacokinetics and Toxicity of High–Dose Intravenous Methotrexate in the Treatment of Leptomeningeal Carcinomatosis, Cancer Chemother Pharmacol, 2000, 46: 19–26.
Conrad, et al., Treatment of Primary and Secondary Progressive Multilple Sclerosis with High Dose Methotrexate and Leucovorin Rescue, Neurology, 1998: 50: A–146.
Mid America Neuroscience Research Foundation, Study Suggests New Hope for Patents Suffering from Progressive Multiple Sclerosis, The Neurology Newsletter, 1998, pp. 1–4.

\* cited by examiner

Primary Examiner—Raymond J. Henley, III
(74) Attorney, Agent, or Firm—Shughart Thomson & Kilroy P.C.

(57) ABSTRACT

The present invention is directed to the treatment of multiple sclerosis by periodically administering a high dose of methotrexate at a level sufficiently high to cross the blood brain barrier. The methotrexate administration is accompanied by leucovorin rescue of the periphery. The high dose methotrexate is preferably administered at 1 to 4 month intervals. The periodic high dose methotrexate treatment may be used in conjunction with interim treatments using a therapeutic agent that is effective in treating MS, but does not cross the BBB in cytotoxic amounts. It is contemplated that the method of the present invention may be employed to treat other non-infectious, non-neoplastic inflammatory conditions of the CNS.

42 Claims, No Drawings

USE OF REGULARLY SCHEDULED HIGH DOSE INTRAVENOUS METHOTREXATE THERAPY, WITH INTERIM ADMINISTRATION OF IMMUNOMODULATORY AGENTS, TO TREAT MULTIPLE SCLEROSIS AND OTHER DISEASES OF THE CENTRAL NERVOUS SYSTEM

CROSS-REFERENCE TO RELATED APPLICATIONS

This application is based on U.S. Provisional Application Ser. No. 60/288,567, filed on May 3, 2001, which is hereby incorporated herein by reference.

STATEMENT REGARDING FEDERALLY SPONSORED RESEARCH OR DEVELOPMENT

Not Applicable.

BACKGROUND OF THE INVENTION

1. Field of the Invention

The present invention is directed to the treatment of non-infectious, non-neoplastic inflammatory conditions of the central nervous system using high dose methotrexate treatments.

2. Description of Related Art

Multiple sclerosis (MS) is a demyelinating disease of the central nervous system (CNS) with unknown cause and no known cure. Though single episodes of demyelination can occur, once the disease is established in multiple sites in the brain, spinal cord, and optic nerves, MS frequently follows a clinically relapsing-remitting course while lesions in the CNS continue to progress. During this phase, an immune mediated inflammatory response to myelin antigens is thought to play a major role in the pathogenesis of developing lesions. Then, in a clinically progressive phase, at least fifty-five percent of patients worsen, with clinical relapses sometimes punctuating their clinical decline.

The mechanism of tissue damage to the CNS is not known with certainty in the progressive phase of MS. It is thought, however, that axonal damage, perhaps through some type of immune mediation, is important in this phase of the disease, though some axonal damage certainly occurs during the inflammatory phase.

Perivascular infiltration of T lymphocytes and macrophages in brain lesions is one of the characteristics of MS. Activation of myelin-reactive T cells in the periphery is an early event in the MS process. These activated T cells facilitate the production by B cells of antibodies against myelin, and activate macrophages to attack oligodendrocytes in the CNS. The functions of these immune cells are regulated by cytokines in autocrine and paracrine fashions. Pro-inflammatory cytokines like IFN-γ, and TNF-α could have disease-promoting roles in MS, whereas anti-inflammatory cytokines, like IL-4, IL-10 and TGF-β, likely down-regulate the disease. The balance between pro-inflammatory and anti-inflammatory cytokines may determine the outcome of injury in MS.

Treatment options for patients with MS are limited. Currently, the primary drugs used to treat MS are interferons and glatiramer acetate. These drugs are marketed under the brand names AVONEX by Biogen, Inc. (interferon-beta-la, recombinant), BETASERON by Berlex Laboratories, Inc. (interferon-beta-1b, recombinant) and CAPOXONE by Teva Neuroscience, LLC (copolymer-1, glatiramer acetate), and are often referred to as the "ABC" treatments. Such treatments have been shown to slow, but not arrest, the clinical course of progression in progressive MS. Thus, alternative, or backup, treatment methods are needed.

Certain chemotherapeutic agents, such as methotrexate, mitoxantrone and cyclophosphamide, have been used to treat MS. Although mitoxantrone and cyclophosphamide have shown some efficacy against the progression of MS, they do not cross the blood brain barrier (BBB) into the CNS and mitoxantrone has limited lifetime use due to toxicity.

Methotrexate is an S-phase chemotherapeutic anti-metabolite, used for the treatment of various neoplasms, particularly CNS lymphoma. Methotrexate is also an anti-inflammatory agent and has been used for the treatment of various autoimmune diseases, such as rheumatoid arthritis and psoriasis. Methotrexate is a folate analogue which competitively binds and inhibits dihydrofolate reductase (DHFR), and thus inhibits the synthesis of thymidine and other compounds requiring methylation for their synthesis by inhibiting the single carbon transfer necessary for their synthetic pathways. Methotrexate also promotes the release of adenosine, and this mechanism may be responsible for its anti-inflammatory activity.

Clinical trials using low-dose methotrexate (7.5 mg/week), administered orally, in progressive MS, have been shown to impact the course of progressive MS with minimal toxicity. This treatment option has been widely adopted in the United States for MS patients in the progressive phase who are developing upper extremity dysfunction. Some MS centers empirically treat refractory patients with higher doses (15 mg or 20 mg) orally once a week. However, when administered orally, the serum level of methotrexate is not sufficient to cross the BBB in cytotoxic amounts. Thus, while oral methotrexate treatments show mild improvement in upper extremity strength in MS patients, a need remains for a treatment that arrests or reverses the progression of the disease.

Methotrexate has been given intravenously in high enough doses to cross the blood-brain barrier (BBB) and enter the CNS. The peripheral bone marrow, immune system, gastrointestinal endothelium and other vital rapidly dividing tissues can be rescued by an inhibitor of methotrexate, such as leucovorin, which does not penetrate the BBB. The safety of high dose methotrexate therapy with leucovorin rescue has been demonstrated. For example, clinical trials using high dose methotrexate (8 g/m$^2$), administered via a four hour intravenous (IV) infusion, with leucovorin rescue, have shown promising results in treating CNS lymphomas with low toxicity. High dose methotrexate (2.5 g/m$^2$) sporadically administered via IV infusion, with leucovorin rescue, has similarly shown no significant toxicity. Further, it is believed no cumulative deficit from repeated treatments has been reported.

BRIEF SUMMARY OF THE INVENTION

The present invention is directed to the treatment of non-infectious, non-neoplastic inflammatory conditions of the CNS by periodically administering a high dose of methotrexate at a level sufficiently high to cross the BBB. Preferably, this periodic high dose treatment is used in conjunction with interim treatments using a therapeutic agent that does not cross the BBB.

In one aspect of the present invention, a high dose of methotrexate is periodically administered to a patient suffering from MS. The periodic high dose methotrexate treatments preferably are supplemented with regular interim treatments using one or more therapeutic agents administered at a level which has therapeutic value in treating MS, but is insufficient to cause the agent to cross the BBB. In any case, the periodic high dose methotrexate treatment must be combined with rescue of the periphery using leucovorin or other methotrexate inhibitor. It has been found that administration of such a treatment regimen to patients with worsening symptoms of progressive MS halted the deterioration of the symptoms in every patient treated, and in some patients, actually resulted in an overall improved score on the multiple sclerosis functional composite (the "MSFC"), a standard clinical outcome measurement for MS.

It is believed that by crossing the BBB and entering the CNS, methotrexate is able to inhibit the mechanism of tissue damage to the CNS in a manner that cannot be achieved with therapeutic agents that do not cross the BBB. Specifically, it is believed that the methotrexate enters the CNS and is able to suppress destructive immune elements resident there, effectively clearing out the CNS of such destructive immune elements. For long-term benefits, the high dose methotrexate must be periodically administered to prevent the destructive inflammatory process from resuming between treatments. Intervals between periodic high dose methotrexate treatments are preferably between about one (1) and about four (4) months, more preferably between about one (1) and about (3) months, and most preferably about two (2) months. The level of methotrexate administered is preferably high enough to achieve cytotoxic levels in the CNS, but low enough to minimize toxicity.

The interim treatments suppress the peripheral immune system between the periodic high dose treatments, thereby further inhibiting the resumption of disease progression. The interim treatments are preferably administered at a dose which has therapeutic value. The interim treatments preferably employ an immunomodulatory agent, such as interferon, glatiramer acetate, low dose oral methotrexate or others.

DETAILED DESCRIPTION OF PREFERRED EMBODIMENT

The present invention provides a method for treating MS, and other non-infectious, non-neoplastic inflammatory conditions of the CNS, by periodically administering a high dose of methotrexate in an amount sufficient to cross the BBB. It is believed the high dose methotrexate purges the CNS of immune cells responsible for the destructive inflammatory process involved in disease formation, thereby inhibiting progression of the disease. However, left unchecked, destructive immune cells from the peripheral immune system will ultimately cross the BBB and repopulate the CNS. Thus, sporadic high dose methotrexate treatments can allow the accumulation of destructive immune cells in the CNS between treatments, which prevents long term inhibition of the disease. By periodically purging the CNS of the destructive immune cells, the periodic high dose treatments of the present invention prevent the disease from progressing and thereby provide long term inhibition of the disease.

The high dose treatments preferably are periodically administered at intervals sufficient to purge the CNS of destructive immune cells and prevent progression of the disease between treatments. The term "periodically" as used herein means that high dose treatments are repeated at regular intervals, as opposed to being repeated, if at all, at sporadic, unscheduled intervals. Preferably high dose treatments are periodically administered at intervals between about one (1) to about four (4) months, more preferably about one (1) to about (3) months, and most preferably the interval between treatments is about (2) months. Most preferably the intervals between treatments are uniform.

The high dose methotrexate is administered by IV infusion at a dosage sufficient to cross the BBB and enter the CNS at a cytotoxic level. Preferably the dose is between about 0.5 and about 4.0 $g/m^2$, more preferably between about 1.0 and about 4.0 $g/m^2$, and most preferably is about 2.0 $g/m^2$. However, lower doses of methotrexate may be used to achieve the effect of a high dose treatment if combined with agents and/or treatments which lower the BBB. After administration of the high dose methotrexate, the peripheral bone marrow, immune system, gastrointestinal endothelium and other vital rapidly dividing tissues can be rescued by an inhibitor of methotrexate, such as leucovorin, which does not penetrate the BBB in a sufficient amount to inhibit the action of the methotrexate within the CNS.

In a particularly preferred embodiment of the present invention, the periodic high dose methotrexate treatments are combined with interim treatments using an immunomodulatory agent that has therapeutic value in treating MS, but does not cross the BBB. The interim treatments serve to modulate the peripheral immune system between high dose treatments. More specifically, the interim treatments, given regularly, presumably suppress the peripheral immune system, and reduce the rate that cells of the immune system cross the BBB into the CNS.

The interim treatments may employ any therapeutic agent that has therapeutic value in treating MS, provided the agent does not cross the BBB in a cytotoxic amount. Preferably the therapeutic agent is an immunomodulatory agent and more preferably is selected from the group consisting of interferon, glatiramer acetate and oral methotrexate. When oral methotrexate is employed as the interim immunomodulatory agent, it is preferably administered at a dosage in the range of 5.0 to 20 mg per week, more preferably 7.5 to 16 mg per week, and most preferably 10 mg per week. Other immunomodulatory agents may be administered at dosages suitable for the treatment of relapsing MS, as can be determined by one in the art. Preferably the interim therapeutic agent may be administered outside of a hospital setting.

The present invention requires that the therapeutic agent be administered at a level which has therapeutic value in treating MS, but is insufficient to cause the agent to cross the BBB in a cytotoxic amount. For some therapeutic agents, no dosage level would be sufficient to cause the agent to cross the BBB due to the molecular weight of the agent. Thus, the interim administration of an agent in relatively high doses is contemplated by the invention, provided that a cytotoxic amount of the agent does not cross the BBB after administration. As used herein the term "low dose" encompasses any dose of a therapeutic agent wherein the agent does not cross the BBB in a cytotoxic amount after administration. Further, although it is contemplated that some interim therapeutic agent may cross the BBB consistent with the present invention, provided it is less than a cytotoxic amount, it is preferred that none of interim therapeutic agent crosses the BBB.

The following example more fully illustrates the present invention:

EXAMPLE 1

Ten patients of relapsing progressive MS were treated with bimonthly high dose intravenous methotrexate with leucovorin rescue, combined with interim treatment with low dose immunomodulatory agents. Patients included in the study had a confirmed diagnosis of secondary progressive MS and at least a three-month history of worsening symptoms. The characteristics of patients enrolled in this study are summarized in Table 1.

TABLE 1

Summary of Patients Enrolled in Methotrexate Treatment

| Number of Patients | Sex Male/ Female | Mean Age Before Methotrexate Treatment (Range) | Mean Duration of MS (Range) | Percent of Patients With Prior A, B, C, M* Drug Treatment | Mean MSFC Before Methotrexate Treatment (Range) |
|---|---|---|---|---|---|
| 10 | 6/4 | 44 (29–56) | 11 years (1–28 years) | 100% | −0.67 (−5.83 to +0.44) |

*A: interferon beta 1a;
B: interferon beta 1b;
C: glatiramer acetate;
M: oral methotrexate.

Methotrexate treatments were given every 2 months for up to 6 treatments. Methotrexate was administered by IV at a dosage of 1 $g/m^2$ for the first three treatments. The drug was well tolerated at dose of 1 $g/m^2$ and some of the patients' MSFC scores improved significantly after 3 treatments. The patients were then switched to doses of 2 $g/m^2$ of methotrexate for three subsequent treatments. Methotrexate was given after hydration and alkalization, with urine pH 7.0 or greater. The infusion was followed by continued hydration for several hours.

Each methotrexate treatment was followed by intravenous leucovorin rescue with 50 mg leucovorin eight hours after the start of the methotrexate infusion. Oral leucovorin (25 mg) was administered every 6 hours for a total of 12 doses after intravenous leucovorin rescue, and the serum methotrexate level measured. If necessary oral leucovorin was continued until the serum level reached 0.05 $\mu M$.

At the time of study entry, all patients were being treated, with interferon (AVONEX® or BETA-SERON®), glatiramer acetate (COPAXONE®), or oral methotrexate. These medications were continued between treatments.

The safety results demonstrate that the treatment is safe. No hematological toxicity was observed. Five patients experienced some nausea with methotrexate treatment, easily treated with Zofran, a standard anti-emetic. Only one patient experienced Grade I renal toxicity after one treatment, whose 2-week follow up creatinine clearance was within acceptable limits and the next treatment was given. No alopecia was noted.

Five samples of cerebrospinal fluid (CSF) were analyzed for methotrexate, representing several patients and several time points after methotrexate infusion of 2 $g/m^2$. The results established that methotrexate did, in fact, cross the BBB in cytotoxic amounts.

The clinical outcome was determined by MSFC scores at baseline and at two months follow up visits after each treatment. The MSFC is a clinical outcome measure, which measures three clinical functions involving hand dexterity, walking, and cognition. Two tailed paired t-test was used to compare the results of MSFC.

Clinical assessment with MSFC scores showed significant improvement after treatment. After one year of treatment, the overall MSFC scores of all the patients showed some increase. The MSFC results, including the three subtests, are shown in Table 2.

TABLE 2

Characteristics of Individual Patients and Effect of Methotrexate on MSFC

| Pts | Sex | Age | Years of MS | Drug Used[a] | 9-HPT baseline | 9-HPT change | 25-ft walk baseline | 25-ft walk change | PASAT baseline | PASAT change | MSFC baseline | MSFC change |
|---|---|---|---|---|---|---|---|---|---|---|---|---|
| 1 | M | 56 | 8 | M | −1.55 | +1.07 | +0.48 | +0.53 | −1.08 | +2.24 | −1.04 | +1.28 |
| 2 | F | 29 | 9 | M | −0.27 | +0.70 | −0.20 | −0.01 | −0.09 | +0.99 | −0.05 | +0.56 |
| 3 | M | 34 | 8 | C | −0.68 | +0.45 | −0.31 | +0.04 | −1.99 | +0.66 | −0.78 | +0.38 |
| 4 | M | 51 | 28 | M | −2.06 | +0.86 | +13.70 | 0.00 | −1.74 | +0.08 | −5.83 | +0.31 |
| 5 | F | 46 | 2 | A | +0.56 | −0.31 | −0.32 | −0.01 | −0.17 | +1.08 | +0.24 | +0.25 |
| 6 | M | 38 | 2 | M | −0.11 | +0.20 | −0.51 | +0.08 | +0.91 | +0.25 | +0.44 | +0.18 |
| 7 | F | 54 | 26 | A | −0.16 | +0.83 | −0.32 | +0.14 | +0.91 | −0.58 | +0.36 | +0.13 |
| 8 | M | 44 | 1 | M | −0.64 | +0.30 | −0.36 | −0.04 | +1.24 | 0.00 | +0.32 | +0.09 |
| 9 | F | 50 | 14 | A | −2.57 | −0.10 | +0.37 | −0.07 | +0.74 | +0.41 | −0.73 | +0.08 |
| 10 | M | 48 | 23 | M | −2.28 | +0.80 | +0.05 | −0.22 | +1.07 | −0.33 | −0.42 | +0.08 |

The patients are listed in decreasing order of improvement as measured by the MSFC. For all the changes, >+0.1 were considered as improvement "(+)", <−0.1 were considered as worsening "(−)" and between −0.1 and +0.1 were considered as unchanged "(o)".
The 9-HPT: nine-hole peg test; 25-ft walk: timed 25-ft walk; PASAT: Paced Auditory Serial Addition Test.

As can be seen from Table 2, the overall MSFC scores of the patients before treatment ranged from −5.83 to +0.44. The maximum increase was +1.28 while the minimum increase was +0.08. The extent of increase did not seem to correlate with MSFC baseline, the duration of MS or other agents used between treatment in this small study. Due to variation between each examination, changes less than 0.1 were considered as unchanged. Thus, seven patients improved and three patients were unchanged on their MSFC after one year of treatment. This is particularly significant, in that all patients had been worsening for at least three months prior to treatment.

Although examination of the subtests showed various results, for each individual patient, at least one subtest of MSFC was improved after treatment. For the nine-hole peg test (arm function), 8 patients improved, 1 patient showed a minor worsening and 1 was unchanged. In the timed 25-ft walk (leg function), 2 patients showed improvement, 1 had a slight worsening and the other 7 remained unchanged. In the PASAT (cognitive function), 6 patients improved, 2 turned worse and the other 2 remained unchanged. In summary, analyzing the patients together, there was significant improvement in mean overall MSFC and nine-hole peg scores after methotrexate treatment (p<0.05). The improvement was not significant in the 25-ft walk and PASAT tests.

The method of the present invention has been shown to stop the progression of MS in subjects suffering from progressive MS. Methotrexate is the preferred therapeutic agent, due to its ability to cross the BBB without disruption of the BBB. Further, methotrexate is inexpensive compared to current MS treatments, is relatively non-toxic when accompanied by leucovorin rescue, and has no established cumulative effects from repeated treatments. Thus, unlike other chemotherapeutic agents employed for the treatment of MS that have limited lifetime use because of toxicity, methotrexate may be administered in high doses over a long period of time.

In view of the success of the treatment regime employed in this study for treating MS, it is contemplated that the same methodology may be valuable in treating other non-infectious, non-neoplastic, inflammatory diseases of the CNS, such as amyotrophic lateral sclerosis (ALS), vasulitis, sarcoid, and the like. Further, it is contemplated that other agents that can be administered at a level sufficient to cross the BBB, and do not produce unacceptable toxicity when administered periodically at such level, may be employed in the present invention.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and sub-combinations are of utility and may be employed without reference to other features and sub-combinations. This is contemplated by and is within the scope of the claims.

What is claimed is:

1. A kit for treating a non-infectious non-neoplastic inflammatory condition of the central nervous system of a human host having a blood brain barrier comprising:
   a dosage of intravenous methotrexate sufficient to cross the blood brain barrier at a cytotoxic level; and
   a plurality of dosages of a second therapeutic agent which has therapeutic value in treating a condition of the central nervous system.

2. The kit of claim 1, further comprising a dosage of a methotrexate inhibitor insufficient to penetrate the blood brain barrier.

3. The kit of claim 1, wherein said second therapeutic agent is an immunomodulatory agent.

4. The kit as claimed in claim 2, wherein said methotrexate inhibitor is leucovorin.

5. A kit of materials for use with periodic methotrexate treatments for treating a non-infectious non-neoplastic inflammatory condition of the central nervous system of a human host having a blood brain barrier, comprising:
   a dosage of intravenous methotrexate sufficient to cross the blood brain barrier at a cytotoxic level; and
   a dosage of a methotrexate inhibitor insufficient to penetrate the blood brain barrier.

6. The kit of claim 5, further comprising a dosage of an immunomodulatory agent.

7. The kit as claimed in 5, wherein said methotrexate inhibitor is leucovorin.

8. A method for treating a non-infectious non-neoplastic inflammatory condition of the central nervous system of a human host having a blood brain barrier comprising;
   periodically administering intravenously at intervals of between about 1 and about 4 months methotrexate to the human host afflicted with the non-infectious non-neoplastic inflammatory condition at a level which is sufficient to cross the blood brain barrier at a cytotoxic level;
   administering to the host, between said periodic administrations of methotrexate, a second therapeutic agent at a second level which has therapeutic value in treating said condition but is insufficient to cause the agent to cross the blood brain barrier in a cytotoxic amount.

9. The method as claimed in claim 1, wherein said periodic administering of methotrexate is conducted at intervals of between about 1 and about 3 months.

10. The method as claimed in claim 1, wherein said second therapeutic agent is an immunomodulatory agent.

11. The method as claimed in claim 10, wherein said periodic administering of methotrexate is conducted at intervals of between about 1 and about 3 months.

12. The method as claimed in claim 1, wherein said second therapeutic agent is selected from the group consisting of interferon, glatiramer acetate and oral methotrexate.

13. The method as claimed in claim 12, wherein said periodic administering of methotrexate is conducted at intervals of between about 1 and about 3 months.

14. The method as claimed in claim 8, 9, or 12, further comprising, the step of administering a dosage of a methotrexate inhibitor insufficient to penetrate the blood brain barrier after said administering of said methotrexate.

15. A method for treating multiple sclerosis in a human host having a blood brain barrier comprising:
   periodically administering intravenously at intervals of between about 1 and about 4 months methotrexate to the human host afflicted with multiple sclerosis at a level which is sufficient to cross the blood brain barrier at a cytotoxic level;
   administering to the host, between said periodic administrations of methotrexate, a second therapeutic agent at a second level which has therapeutic value in treating multiple sclerosis but is insufficient to cause the agent to cross the blood brain barrier in a cytotoxic amount.

16. The method as claimed in claim 15, wherein said periodic administering of methotrexate is conducted at intervals of between about 1 and about 3 months.

17. The method as claimed in claim 15, wherein said periodic administering or methotrexate is conducted at intervals of about 2 months.

18. The method as claimed in claim 15, wherein said second therapeutic agent is an immunomodulatory agent.

19. The method as claimed in claim 17, wherein said second therapeutic agent is an immunomodulatory agent.

20. The method as claimed in claim 16, wherein said second therapeutic agent is an immunomodulatory agent.

21. The method as claimed in claim 15, 16, or 17, further comprising, the step of administering a dosage of a methotrexate inhibitor insufficient to penetrate the blood brain barrier after said administering of said methotrexate.

22. The method as claimed in claim 21, wherein said methotrexate inhibitor is leucovorin.

23. A method for treating a non-infectious non-neoplastic inflammatory condition of the central nervous system of a human host having a blood brain barrier comprising:
periodically administering intravenously methotrexate at intervals of between about 1 and about 4 months to the human host afflicted with a non-infectious non-neoplastic inflammatory condition of the central nervous system; and
using a dosage of methotrexate at each administration thereof, which is sufficient to cross the blood brain barrier at a cytotoxic level.

24. The method as claimed in claim 23, wherein said periodic administering of methotrexate is conducted at intervals of between about 1 and about 3 months.

25. The method as claimed in claim 23, wherein said periodic administering of methotrexate is conducted at intervals of about 2 months.

26. The method as claimed in claim 23, 24, or 25 wherein said dosage ranges from about 1 $g/m^2$ to about 4 $g/m^2$.

27. The method as claimed in claim 23, wherein said condition is multiple sclerosis.

28. The method as claimed in claim 23, 24, 25, or 27 further comprising, administering a dosage of a methotrexate inhibitor insufficient to penetrate the blood brain barrier after said administering of said methotrexate.

29. The method as claimed in claim 23, further comprising administering to said host, between said periodically administering of methotrexate, a second therapeutic agent at a second level which has therapeutic value in treating said condition.

30. The method as claimed in claim 29, further comprising, administering a dosage of a methotrexate inhibitor insufficient to penetrate the blood brain barrier after said step of administering methotrexate.

31. The method as claimed in claim 28, wherein said methotrexate inhibitor is leucovorin.

32. The method as claimed in claim 30, wherein said methotrexate inhibitor is leucovorin.

33. The method as claimed in claim 26 further comprising the step of administering a dosage of a methotrexate inhibitor insufficient to penetrate the blood brain barrier after said step of administering methotrexate.

34. A method for treating a non-infectious non-neoplastic inflammatory condition of the central nervous system of a human host having a blood brain barrier comprising:

(i) periodically administering intravenously methotrexate to a human host afflicted with a non-infectious non-neoplastic inflammatory condition at a level which is sufficient to cross the blood brain barrier at a cytotoxic level; and (ii) administering to said host a second therapeutic agent at a second level which has therapeutic value in treating said condition.

35. The method as claimed in claim 34, further comprising the steps of:
reperforming said administering of methotrexate after said administering said second therapeutic agent; and
readministering said second therapeutic agent after said reperforming said administering of methotrexate.

36. The method as claimed in claim 35, wherein said condition is multiple sclerosis.

37. The method as claimed in claim 35, wherein said second therapeutic agent is an immunomodulatory agent.

38. The method as claimed in claim 35, further comprising, administering a dosage of a methotrexate inhibitor insufficient to penetrate the blood brain barrier after said administering of said methotrexate.

39. The method as claimed in claim 38, wherein said methotrexate inhibitor is leucovorin.

40. A method for treating a non-infectious non-neoplastic inflammatory condition of the central nervous system of a human host having a blood brain barrier comprising the steps of:
periodically administering methotrexate intravenously at a level which is sufficient to cross the blood brain barrier at a cytotoxic level; and
dosing, after said administration of methotrexate, with an amount of a methotrexate inhibitor which is insufficient to penetrate the blood brain barrier.

41. The method as claimed in 40, wherein said methotrexate inhibitor is leucovorin.

42. A method for treating multiple sclerosis in a human host having a blood brain barrier comprising:
periodically administering methotrexate intravenously at a level which is sufficient to cross the blood brain barrier at a cytotoxic level to the human host afflicted with multiple sclerosis; and
dosing the host, after said administration of methotrexate, with an amount of leucovorin insufficient to penetrate the blood brain barrier.

* * * * *